United States Patent [19]

Arai et al.

[11] 3,933,874

[45] Jan. 20, 1976

[54] METHOD FOR PREPARING OF β-ANILINO-β-HYDRAZINOACRYLATES

[75] Inventors: Atsuaki Arai, Minami-ashigara; Daijiro Nishio, Odawara; Mitsugu Tanaka, Minami-ashigara; Yoshikazu Fujita; Hisao Suzuki, both of Odawara, all of Japan

[73] Assignee: Fuji Photo Film Co., Ltd., Minami-ashigara, Japan

[22] Filed: Dec. 13, 1974

[21] Appl. No.: 532,577

[30] Foreign Application Priority Data

Dec. 13, 1973 Japan.............................. 48-140963

[52] U.S. Cl............ 260/404.5; 260/470; 260/471 A
[51] Int. Cl.².................. C09F 7/00; C07C 149/40; C07C 79/46
[58] Field of Search............. 260/471 A, 404.5, 470

[56] References Cited
UNITED STATES PATENTS

| | | | |
|---|---|---|---|
| 2,680,731 | 6/1954 | Martin | 260/470 X |
| 3,406,165 | 10/1968 | Kruckenberg | 260/471 A X |
| 3,660,438 | 5/1972 | Dexter | 260/404.5 |
| 3,835,164 | 9/1974 | Widdig et al. | 260/471 C X |

FOREIGN PATENTS OR APPLICATIONS

| | | | |
|---|---|---|---|
| 6,700,417 | 7/1967 | Netherlands | 260/471 A |
| 512,257 | 10/1971 | Switzerland | 260/471 A |

*Primary Examiner*—Winston A. Douglas
*Assistant Examiner*—William G. Wright
*Attorney, Agent, or Firm*—Sughrue, Rothwell, Mion, Zinn & Macpeak

[57] ABSTRACT

A method for the preparation of a β-anilino-β-hydrazinoacrylate which comprises reacting a β-anilino-β-alkoxyacrylate with a hydrazine. β-Anilino-β-hydrazinoacrylates are valuable intermediates in preparing 3-anilino-5-pyrazolone magenta color-forming couplers and the method of the present invention can be applied particularly to the preparation of 3-anilino-5-pyrazolones which have a hydrophobic group on the anilino group.

7 Claims, No Drawings

3,933,874

METHOD FOR PREPARING OF β-ANILINO-β-HYDRAZINOACRYLATES

BACKGROUND OF THE INVENTION

1. Field of the Invention

The present invention relates to a method for the preparation of a β-anilino-β-hydrazinoacrylate which comprises reacting a β-anilino-β-alkoxyacrylate with a hydrazine, and to a method for preparation of a 3-anilino-5-pyrazolone using the β-anilino-β-hydrazinoacrylate.

2. Description of the Prior Art

3-Anilino-5-pyrazolones are valuable compounds useful as intermediates of dyes and as photographic magenta color-forming couplers. Of the 3-anilino-5-pyrazolones, compounds which have a substituent such as a halogen atom, an alkyl group or an alkoxy group in the 2-position of the 3-anilino group and a hydrophobic group containing 6 or more carbon atoms on the 3-anilino group are particularly useful for magenta color-forming couplers in view of their superior photographic properties.

Several methods of preparing 3-anilino-5-pyrazolones have heretofore been provided. However these methods have defects in that the reaction steps are complicated, the yields of the products are low, expensive agents are used in the reaction, and the like. Of these methods, the method described in British Pat. No. 1,129,333 in which a β-anilino-β-alkoxyacrylate is reacted with a hydrazine in the presence of an alkali metal alkoxide is the most useful, but the yields of the product are still unsatisfactory. In particular, when the method is applied to the preparation of 5-pyrazolones having a hydrophobic group on the anilino group as described above, the desired 3-anilino-5-pyrazolones can not be obtained or is obtained in extremely low yields.

The reactions of conventional methods have now been investigated in great detail and it has been found that when a β-anilino-β-alkoxyacrylate is reacted with a hydrazine, a subsidiary reaction in which the anilino group attached to the β-position of the β-anilino-β-alkoxyacrylate is released proceeds simultaneously to lead to the formation of a complicated reaction mixture. As a result, when such is followed with a ring closing reaction in which an alkali and the like is added to the reaction mixture, the desired 3-anilino-5-pyrazolone is obtained in very low purity and poor yields. In particular, when a compound in which the anilino group has a hydrophobic group is used, isolation and purification of the desired compound is extremely difficult and therefore almost none of the desired compound can be obtained.

SUMMARY OF THE INVENTION

It is thus an object of the present invention to provide β-anilino-β-hydrazinoacrylates.

Another object of the present invention is to provide a method for the preparation of β-anilino-β-hydrazinoacrylates in high yields.

A further object of the present invention is to provide an improved method for the preparation of 3-anilino-5-pyrazolones.

A still further object of the present invention is to provide a method for the preparation of 3-anilino-5-pyrazolones with ease and in high yields.

An even further object of the present invention is to provide a method for preparation of 3-anilino-5-pyrazolones having a hydrophobic group on the 3-anilino group with ease and in high yields.

These and other objects of the present invention will become apparent from the following detailed description and examples as set forth below.

The objects of the invention are accomplished with a process for preparing a β-anilino-β-hydrozinoacrylate which comprises reacting a β-anilino-β-alkoxyacrylate with a hydrazine, and a process for preparing a 3-anilino-5-pyrazolone which comprises using the β-anilino-β-hydrazinoacrylate as an intermediate.

DETAILED DESCRIPTION OF THE INVENTION

In accordance with the present invention, 3-anilino-5-pyrazolones pyrazolines can be obtained in high yields by reacting β-anilino-β-alkoxyacrylates with hydrazines and separating β-anilino-β-hydrazinoacrylates as intermediates.

By the reaction of β-anilino-β-alkoxyacrylate with hydrazine according to the present invention, the hydrazine is introduced into the β-position of the β-anilino-β-alkoxyacrylate in place of the alkoxy group to produce a β-anilino-β-hydrazinoacrylate. This compound can be easily isolated and purified.

Of the β-anilino-β-hydrazinoacrylates which can be prepared by the present invention, the compounds represented by the following general formula (I)

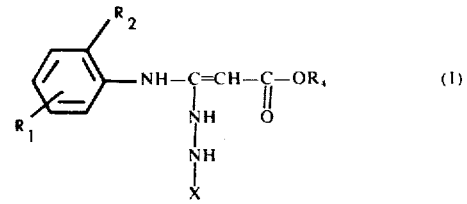

wherein $R_1$ represents an acylamino group, an alkylsulfamoyl group, an arysulfamoyl group or an alkoxycarbonyl group; $R_2$ represents a halogen atom, an alkyl group or an alkoxy group; $R_4$ represents an alkyl group; and X represents an aryl group; are particularly useful as intermediates of magenta color-forming couplers.

The group represented by $R_1$ in the general formula (I) preferably includes 6 or more carbon atoms, particularly 8 to 26 carbon atoms. The alkyl moiety and the aryl moiety included in $R_1$ can be substituted.

Suitable acylamino groups, alkylsulfamoyl groups, arylsulfamoyl groups and alkoxycarbonyl groups represented by R in the general formula (I) are acylamino groups such as hexanoylamino, octanoylamino, decanoylamino, hexadecanoylamino, octadecanoylamino, 2,4-di-tert-pentylphenoxyacetamido, 2-(2,4-di-tert-pentylphenoxy)butyramido, 4-(3-pentadecylphenoxy)butyramido, etc., alkylsulfamoyl groups such as cyclohexylsulfamoyl, dodecylsulfamoyl, 1,1-dimethylhexadecylsulfamoyl, 3-(2,4-di-tert-pentylphenoxy)propylsulfamoyl, 4-(3-pentadecylphenoxy)butylsulfamoyl, 2-(dodecylsuccinimido)ethylsulfamoyl, N-methyl-N-octadecylsulfamoyl, etc., arylsulfamoyl groups such as phenylsulfamoyl, 4-methylphenylsulfamoyl, 4-dodecylphenylsulfamoyl, and alkoxycarbonyl groups such as hexyloxycarbonyl, dodecyloxycarbonyl, -tetradecyloxycarbonyl, 2-(2,4-di-tert-pentylphenoxy)ethoxycarbonyl, 4-(2,4-di-tert-pentylphenoxy)-butoxycarbonyl, 2-(3-tert-butyl-4-hydroxyphenoxy)tetradecyloxycarbonyl, 2-dodecyloxycarbonylethoxycarbonyl, etc.

For $R_2$ in the general formula (I), suitable halogen atoms include fluorine, chlorine, bromine and the like, and suitable alkyl groups and alkoxy groups include those groups containing 1 to 8 carbon atoms. Suitable examples of alkyl groups and alkoxy groups for $R_2$ are alkyl groups such as methyl, ethyl, butyl, hexyl, etc., and alkoxy groups such as methoxy, ethoxy, butoxy, hexyloxy, etc. A chlorine atom, alkyl groups having 1 to 4 carbon atoms and alkoxy groups having 1 to 4 carbon atoms are particularly preferred as $R_2$.

Suitable aryl groups represented by X in the general formula (I) include substituted or unsubstituted phenyl groups.

Preferred substituents of the alkyl moiety of $R_1$ include halogen atoms (such as chlorine, bromine, fluorine, etc.) alkoxy groups (such as methoxy, ethoxy, butoxy, octyloxy, etc.), acyl groups (such as acetyl, propionyl, etc.), alkoxycarbonyl groups (such as methoxycarbonyl, ethoxycarbonyl, hexadecyloxycarbonyl, etc.), a carboxyl group, a sulfo group, a nitro group, amino groups, acylamino groups (such as acetamido, butyramido, 2-(2,4-di-tertpentylphenoxy)-butyramido, benzamido, etc.), sulfonamido groups (such as methylsulfonamido, phenylsulfonamido, etc.), ureido groups (such as methylureido, phenylureido, etc.) and a cyano group. Preferred substituents of the aryl moiety of $R_1$ and the phenyl group of X include halogen atoms (such as chlorine, bromine, fluorine, etc.), alkyl groups (such as methyl, ethyl, butyl, octyl, trifluoromethyl, etc.), alkoxy groups (such as methoxy, ethoxy, butoxy, octyloxy, etc.), acyl groups (such as acetyl, propionyl, etc.), alkoxycarbonyl groups (such as methoxycarbonyl, ethoxycarbonyl, hexadecyloxycarbonyl, etc.), a carboxyl group, a sulfo group, a nitro group, amino groups, a cylamino groups (such as acetamido, butyramido, 2-(2,4-di-tert-pentylphenoxy)-butyramido, benzamido, etc.), sulfonamido groups (such as methylsulfonamido, phenylsulfonamido, etc.), ureido groups (such as methylureido, phenylureido, etc.) and a cyano group.

According to the method of the present invention, the β-anilino-β-hydrazinoacrylates represented by the general formula (I) can be prepared by reacting β-anilino-β-alkoxyacrylates represented by the general formula (II)

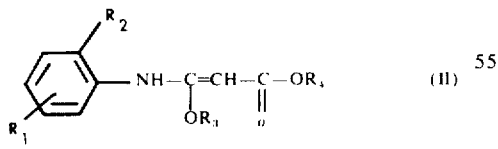
(II)

with the arylhydrazines represented by the general formula (III)

(III)

wherein $R_1$, $R_2$, $R_4$ and X are the same as defined in the general formula (I), and $R_3$ represents an alkyl group.

In the general formulas (II) and (III), $R_1$, $R_2$ and X represent the same meanings as in general formula (I), and $R_3$ and $R_4$ each represents an alkyl group which may be the same or different from each other. Suitable alkyl groups represented by $R_3$ and $R_4$ in the formula (II) include those having 1 to 8 carbon atoms, for example, alkyl groups such as methyl, ethyl, butyl, hexyl, etc. Alkyl groups having 1 to 4 carbon atoms are particularly preferred for $R_3$ and $R_4$.

The β-anilino-β-alkoxyacrylates represented by the general formula (II) which are used in the present invention can be prepared by the methods described in British Pat. No. 1,129,344, French Pat. No. 1,469,360, U.S. Pat. No. 3,798,234, and Japanese Patent Application No. 87726/73, etc. As an example, the synthesis of ethyl β-(2-chloro-5-tetradecanoylaminoanilino)-β-ethoxyacrylate is specifically illustrated below.

SYNTHESIS EXAMPLE 1

A mixture of 40 g of ethyl β-imino-β-ethoxypropionate hydrochloride, 40 g of 2-chloro-5-tetradecanoylaminoaniline and 150 ml of ethanol was reacted by heating at 50°C for 4 hours with stirring. After the reaction mixture was filtered, water was added to the filtrate and the filtrate was extracted with ethyl acetate. By distilling off the ethyl acetate, a residue which was the almost pure desired compound was obtained. The yield was 54 g (96%). The melting point of the compound recrystallized from atcetonitrile was 58° to 59°C.

SYNTHESIS EXAMPLE 2

A mixture consisting of 20.7 g of ethyl β,β-diethoxyacrylate and 38.2 g of 2-chloro-5-tetradecanoylaminoaniline was reacted by heating in nitrogen gas at 110°C for 4 hours with stirring. The crystals were collected from the reaction mixture and recrystallized from acetonitrile to obtain 44.5 g (90%) of the desired compound having a melting point of 58° to 59°C.

Typical examples of β-anilino-β-alkoxyacrylates are illustrated below.

1. Ethyl β-(2-chloro-5-tetradecanoylaminoanilino)-β-ethoxyacrylate
2. Ethyl β-(2-methoxy-5-tetradecanoylaminoanilino)-β-ethoxyacrylate
3. Methyl β-(2-chloro-5-octadecanoylaminoanilino)-β-methoxyacrylate
4. Ethyl β-(2-methoxy-5-decanoylaminoanilino)-β-ethoxyacrylate
5. Ethyl β-(2-chloro-5-hexadecanoylaminoanilino)-β-ethoxyacrylate
6. Butyl β-{2-methoxy-5-[2-(2,4-di-tert-pentylphenoxy)butyramido]-anilino}-β-methoxyacrylate
7. Ethyl β-(2-chloro-4-tetradecylsulfamoylanilino)-β-ethoxyacrylate
8. Ethyl β-(2-chloro-5-tetradecylsulfamoylanilino)-β-ethoxyacrylate
9. Ethyl β-(2-chloro-5-dodecylsulfamoylanilino)-β-ethoxyacrylate
10. Ethyl β-[2-chloro-5-(1,1-dimethylhexadecylsulfamoyl)anilino]-β-ethoxyacrylate
11. Ethyl β-(2-octyloxy-5-cyclohexylsulfamoylanilino)-β-ethoxyacrylate
12. Methyl β-{2-chloro-5-[3-(2,4-di-tert-pentylphenoxy)propylsulfamoyl]anilino}-β-ethoxyacrylate
13. Ethyl β-{2-chloro-5-[3-(3-pentadecylphenoxy)propylsulfamoyl]-anilino}-β-ethoxyacrylate
14. Ethyl β-{2-chloro-5-[4-(3-pentadecylphenoxy)butylsulfamoyl]-anilino}-β-ethoxyacrylate 15. Ethyl β-{2-chloro-5-[2-(dodecylsuccinimido)ethylsulfamoyl]-anilino}-β-ethoxyacrylate
16. Ethyl β-{2-chloro-4-[2-(3-tert-butyl-4-hydroxyphenoxy)-tetradecylsulfamoyl]anilino}-β-ethoxyacrylate
17. Ethyl β-{2-chloro-5-[N-(2-cyanoethyl)-N-hexadecylsulfamoyl]-anilino}-β-ethoxyacrylate
18. Ethyl β-{2,5-dichloro-4-[3-(2,4,-di-tert-pentylphenoxy)-propylsulfamoyl]anilino}-β-ethoxyacrylate
19. Ethyl β-{2-methoxy-5-[3-(2,4-di-tert-pentylphenoxy)propylsulfamoyl]anilino}-β-ethoxyacrylate
20. Ethyl β-(2-methoxy-5-tetradecylsulfamoylanilino)-β-ethoxyacrylate
21. Ethyl β-[2-chloro-5-(N-methyl-N-octadecylsulfamoyl)anilino]-β-ethoxyacrylate
22. Ethyl β-{2-chloro-5-[(4-dodecyl)phenylsulfamoyl]amilino}-β-ethoxyacrylate
23. Methyl β-(2-methyl-5-dodecylsulfamoylanilino)-β-ethoxyacrylate
24. Ethyl β-{2-chloro-5-[2-(N-butylhexadecylamido)ethylsulfamoyl]-anilino}-β-ethoxyacrylate
25. Ethyl β-(2,5-dichloro-4-cyclohexylsulfamoylanilino)-β-ethoxyacrylate
26. Ethyl β-(2-chloro-5-tetradecyloxycarbonylanilino)-β-ethoxyacrylate
27. Ethyl β-(2-methyl-5-tetradecyloxycarbonylanilino)-β-ethoxyacrylate
28. Ethyl β-{2-methoxy-5-[2-(2,4-di-tert-pentylphenoxy)ethoxycarbonyl]anilino}-β-ethoxyacrylate
29. Ethyl β-{2-chloro-5-[2-(2-dodecylsuccinimido)ethoxycarbonyl]-anilino}-β-ethoxyacrylate
30. Ethyl β-[2-chloro-5-(2-butoxytetradecyloxycarbonyl)anilino]-β-ethoxyacrylate
31. Ethyl β-{2-methyl-5-[4-(2,4-di-tert-pentylphenoxy)butoxycarbonyl]anilino}-β-ethoxyacrylate
32. Ethyl β-{2-chloro-5-[2-(3-pentadecylphenoxy)ethoxycarbonyl]-anilino}-β-ethoxyacrylate
33. Ethyl β-{2-chloro-5-[2-(3-tert-butyl-4-hydroxyphenoxy)tetradecyloxycarbonyl]anilino}-β-ethoxyacrylate
34. Ethyl β-[2-methoxy-5-(2-hexyldecyloxycarbonyl)anilino]-β-ethoxyacrylate
35. Ethyl β-[2-chloro-4-(2-dodecyloxycarbonylethoxycarbonyl)-anilino]-β-ethoxyacrylate
36. Ethyl β-[2-methoxy-5-(tetradecyloxycarbonylmethoxycarbonyl)-anilino]-β-ethoxyacrylate The hydrazines, particularly, the arylhydrazines, which are used in the present invention can be prepared by known methods.

Typical examples of hydrazines are illustrated below.
1. Phenylhydrazine
2. 2-Chlorophenylhydrazine
3. 4-Chlorophenylhydrazine
4. 4-Bromophenylhydrazine
5. 4-Fluorophenylhydrazine
6. 2,5-Dichlorophenylhydrazine
7. 2,6-Dichlorophenylhydrazine
8. 3,5-Dibromophenylhydrazine
9. 2,4,6-Trichlorophenylhydrazine
10. 2,4,6-Tribromophenylhydrazine
11. 2-Cyanophenylhydrazine
12. 4-Cyanophenylhydrazine
13. 3-Nitrophenylhydrazine
14. 4-Aminophenylhydrazine
15. 4-Methylaminophenylhydrazine
16. 4-Acetamidophenylhydrazine
17. 4-[2-(2,4-Di-tert-pentylphenoxy)butyramido]-phenylhydrazine
18. 2,6-Dimethylphenylhydrazine
19. 2,6-Diethylphenylhydrazine
20. 2-Trifluoromethylphenylhydrazine
21. 4-Methoxyphenylhydrazine
22. 2-Ethoxyphenylhydrazine
23. 4-Phenylphenylhydrazine
24. 4-Phenoxyphenylhydrazine
25. 4-Butylphenylhydrazine
26. 4-(N-Methylbenzamido)phenylhydrazine
27. 3-(N,N-Diethylcarbamoyl)phenylhydrazine
28. 4-(N-methylphenylsulfanamido)phenylhydrazine
29. 4-Methylureidophenylhydrazine
30. 3-Acetylphenylhydrazine
31. 2-Methyl-5-nitrophenylhydrazine
32. 2-Chloro-5-cyanophenylhydrazine
33. 2-Methyl-5-chlorophenylhydrazine
34. 2,6-Dichloro-4-methylphenylhydrazine
35. 2,6-Dichloro-4-methoxyphenylhydrazine
36. 2,4-Dichloro-6-methylphenylhydrazine
37. 2-Chloro-4,6-dimethylphenylhydrazine
38. 2,6-Dichloro-4-nitrophenylhydrazine
39. 2,4,6-Trimethyl-3-nitrophenylhydrazine
40. 2,4,6-Trimethyl-3-acetamidophenylhydrazine
41. 2,5-Dicarboxyphenylhydrazine
42. 4-Ethoxycarbonylphenylhydrazine
43. 2,6-Dichloro-4-tetradecyloxycarbonylphenylhydrazine
44. 4-(N,N-Dimethylsulfamoyl)phenylhydrazine
45. 3-Sulfo-4-phenoxyphenylhydrazine
46. 2-Methoxy-5-methyl-3,4,6-trichlorophenylhydrazine
47. 3-Dimethylamino-4-bromophenylhydrazine
48. Naphthylhydrazine
49. Butylhydrazine
50. Cyclohexylhydrazine
51. 2-Benzothiazolylhydrazine The reaction of the β-anilino-β-alkoxy acrylates with the hydrazines can usually be carried out in the absence of a solvent. However an inert solvent can be used, if desired. Preferred inert solvents are those capable of dissolving the reactants and having a boiling point of about 50°C or higher. Examples of such solvents include methanol, ethanol, propanol, butanol, benzene, chlorobenzene, xylene, ethylene glycol monomethyl ether, ethylene glycol monoethyl ether, tetrahydrofuran and dioxane. In general, the reaction is carried out under heating at a temperature ranging from about 50°C to about 200°C. Although the preferred reaction temperature can advantageously be varied over a wide range due to the reactants, generally a temperature from 80° to 120°C is suitable. Preferably the reaction is carried out in an inert gas such as nitrogen gas, argon gas, and at a slightly reduced pressure in order to prevent coloration of the reaction products.

The ratios of the amount of the reactants used in the reaction are not limited and can vary. However, good results can usually be obtained when the hydrazines are used in a range of from about 0.5 to about 2.5 moles, preferably 1 to 1.3 moles, per mole of the β-anilino-β-alkoxyacrylates.

The reaction of the β-anilino-β-alkoxyacrylates with the hydrazines can be carried out in the presence or absence of a catalyst. For example, a compound having a pKa ranging from about 5 up to less than 14 can be advantageously used to control side reactions and to produce the desired β-anilino-β-hydrazinoacrylates in high yields. Compounds having a pKa of 8 to less than 14 are particularly useful. Most preferred compounds are those compounds having a pKa of 9 to 11. Although the amount of such a compound is not particularly limited, preferred results are usually obtained when the compound is used at about 0.1 to about 10 moles, preferably 0.5 to 5 moles. per mole of the β-anilino-β-alkoxyacrylates.

Specific examples of compounds having a pKa ranging from about 5 up to less than 14 which can be used in the present invention include phenol, o-, m- and p-cresol, o-, m- and p-chlorophenol, o-, m- and p-fluorophenol, o-, m- and p-bromophenol, o- and p-nitrophenol, 2,3-, 2,4-, 2,5-, 2,6-, 3,4- and 3,5-dimethyl phenol, 2,5- and 3,4-dinitrophenol, 2,3,5- and 2,4,6-trimethylphenol, o-, m- and p-methoxyphenol, tert-butylphenol, hydroquinone, catechol, resorcinol, methylhydroquinone, tertbutylhydroquinone, n-octylhydroquinone, 2,5-di-tert-butylhydroquinone, p-toluidine, α-, β- and γ-picoline, naphthol, boric acid, and the like.

The β-anilino-β-hydrazinoacrylates are easily subjected to a ring closing reaction using a strong alkali such as an alkali metal or alkaline earth metal hydroxide such as sodium hydroxide, potassium hydroxide, barium hydroxide, etc. or an alkali metal alkoxide such as sodium ethoxide, potassium butoxide, etc., to form the corresponding 3-anilino-5-pyrazolones. The reaction can be carried out at a temperature of about −10° to 50°C, preferably 0° to 30°C, in the presence of an inert solvent, for example, the inert solvents as described hereinbefore. A suitable amount of the strong alkali can range from about 0.5 to 10 moles, preferably 1 to 2 moles, per mole of the β-anilino-β-hydrazino-acrylates. The reaction can be carried out at normal pressure and preferably is conducted in an inert atmosphere such as a nitrogen, argon, etc. atmosphere.

For instance, the 3-anilino-5-pyrazolones represented by the general formula (IV)

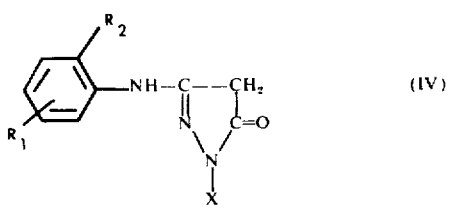

(IV)

wherein R₁, R₂ and X are the same as defined in the general formula (I) can be prepared using the β-anilino-β-hydrazinoacrylates represented by the general formula (I), for example, using the method disclosed in applicants' U.S. Pat. application Ser. No. 519,310, filed Oct. 30, 1974.

An important advantage of the present invention is that the preparation of the 3-anilino-5-pyrazolones having a hydrophobic group in the 3-anilino group which cannot be prepared or can be prepared with difficulty using known methods can be carried out easily and in high yields.

In order to prepare 3-anilino-5-pyrazolones having a hydrophobic group in the 3-anilino group a method in which a 3-anilino-5-pyrazolone is prepared and a hydrophobic group is introduced thereto is also known. For example, 1-phenyl-3-(2-chloro-5-tetradecanoylaminoanilino)-5-pyrazolone can be prepared by reacting ethyl β-alkoxy-β-(2-chloro-5-nitroanilino)acrylate with phenylhydrazine to prepare 1-phenyl-3 -(2-chloro-5-nitroanilino)-5-pyrazolone, converting this compound to 1-phenyl-3-(2-chloro-5-aminoanilino)-5-pyrazolone by reduction, and after purifing sufficiently, reacting it with tetradecanoic chloride. However, this method is quite inferior to the method of the present invention in view of the complicated reaction steps and yields.

The present invention will now be explained in greater detail by reference to the following examples. Unless otherwise indicated, all parts, percents, ratios and the like are by weight.

EXAMPLE 1

A mixture of 50 g of ethyl β-(2-chloro-β-5-tetradecanoylaminoanilino)-β-ethoxyacrylate, 25 g of 2,4,6-trichlorophenylhydrazine and 50 g of phenol (pKa : 9.998) was heated at 100°C for 8 hours under a reduced pressure of 25 to 30 mmHg with stirring. To the reaction mixture 200 ml of acetonitrile was added and the mixture was cooled with water to deposit crystals. The crystals were collected by filtration and washed with cool acetonitrile to obtain 54 g of ethyl β-(2-chloro-5-tetradecanoylaminoanilino)-β-(2,4,6-trichlorophenylhydrazino)acrylate which was white and substantially pure. The melting point was 91° to 93°C.

The structure of the compound was determined by its infrared absorption spectrum and mass spectrum of M⁺ 658 (Calculated 658).

Elemental Analysis

Found: C 56.36%, H 6.43%, N 8.73%

Calculated: C 56.37%, H 6.41%, N 8.48%

EXAMPLE 2

Using o-cresol (pKa : 10.287) instead of the phenol used in Example 1, the reaction was carried out by heating at 100°C for 8 hours under a reduced pressure of 25 to 30 mmHg with stirring. The desired compound was obtained in a yield of 84%.

EXAMPLE 3

Using 2,4,6-trichlorophenol (pKa: 6.41) instead of the phenol used in Example 1, the reaction was carried out by heating at 100°C for 2.5 hours under a reduced pressure of 25 to 30 mmHg with stirring. The desired compound was obtained in a yield of 49%.

EXAMPLE 4

Without using the acidic compound as described in the foregoing examples, the reaction was carried out by heating at 100°C for 7 hours under a reduced pressure of 25 to 30 mmHg with stirring. The desired compound was obtained in a yield of 43%.

EXAMPLE 5

To 13.2 g of the acrylate obtained in Example 1, 40 ml of methanol and 1.6 g of sodium hydroxide were added, and the mixture was stirred for 10 minutes in a water bath. The reaction mixture was then poured into about 100 ml of ice water, and neutralized with acetic acid to deposite white crystals which were collected by filtration. The crystals obtained were substantially pure 1-(2,4,6-trichlorophenyl)-3-(2-chloro-5-tetradecanoylaminoanilino)-5-pyrazolone. The yield was 12.1 g (98%). The melting point of the compound recrystallized from a solvent mixture of ethyl acetate and n-hexane (volume ratio 1:1) was 92° to 96°C.

EXAMPLE 6

In the same manner as described in Example 5 but using ethyl β-{2-chloro-5-[2-(2,4-di-tert-pentylphenoxy)butyramido]-anilino}-β-(2,6-di-chloro-4-methoxyphenylhydrazino)acrylate, 1-(2,6-di-chloro-4-methoxyphenyl)-3-{2-chloro-5-[2-(2,4-di-tertpentylphenoxy)butyramido]anilino}-5-pyrazolone was obtained in an almost quantitative yield. The melting point of the compound recrystallized from ethanol was 176° to 177°C.

EXAMPLE 7

In the same manner as described in Example 5 but using ethyl β-{2-chloro-5-[3-(2,4-di-tert-pentylphenoxy)propylsulfamoyl]-anilino}-β-(2,4,6-trichlorophenylhydrazino)acrylate, 1-(2,4,6-trichlorophenyl)-3-{2-chloro-5-[3-(2,4-di-tert-pentylphenoxy)-propylsulfamoyl]anilino}-5-pyrazolone was obtained in an almost quantitative yield. The melting point of the compound recrystallized from ethanol was 173° to 175°C.

EXAMPLE 8

In the same manner as described in Example 5 but using ethyl β-(2-methoxy-5-tetradecyloxycarbonylanilino)-β-(2,4,6-trichlorophenylhydrazino)acrylate, 1-(2,4,6-trichlorophenyl)-3-(2-methoxy-5-tetradecyloxycarbonylanilino)-5-pyrazolone was obtained in an almost quantitative yield. The melting point of the compound recrystallized from methanol was 110° to 112°C.

While the invention has been described in detail and with reference to specific embodiments thereof, it will be apparent to one skilled in the art that various changes and modifications can be made therein without departing from the spirit and scope thereof.

What is claimed is:

1. A β-anilino-β-hydrazinoacrylate represented by the following general formula (I)

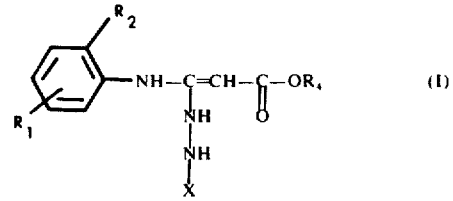

wherein $R_1$ represents an acylamino group, an alkylsulfamoyl group, an arylsulfamoyl group or an alkoxycarbonyl group; $R_2$ represents a halogen atom, an alkyl group or an alkoxy group; $R_4$ represents an alkyl group; and X represents an aryl group.

2. The β-anilino-β-hydrazinoacrylate as claimed in claim 1, wherein $R_1$ contains 6 or more carbon atoms.

3. The β-anilino-β-hydrazinoacrylate as claimed in claim 1, wherein $R_1$ contains 8 to 26 carbon atoms.

4. The β-anilino-β-hydrazinoacrylate as claimed in claim 1, wherein said alkyl group for $R_2$ contains 1 to 8 carbon atoms.

5. The β-anilino-β-hydrazinoacrylate as claimed in claim 1, wherein said alkoxy group for $R_2$ contains 1 to 8 carbon atoms.

6. The β-anilino-β-hydrazinoacrylate as claimed in claim 1, wherein said alkyl group for $R_4$ contains 1 to 8 carbon atoms.

7. The β-anilino-β-hydrazinoacrylate as claimed in claim 1, wherein said aryl group is a phenyl group or a substituted phenyl group in which the substituent is one or more of a halogen atom, an alkyl group, an alkoxy group, an acyl group, an alkoxycarbonyl group, a carboxy group, a sulfo group, a nitro group, an amino group, an acylamino group, a sulfonamido group, a ureido group and a cyano group.

* * * * *

UNITED STATES PATENT AND TRADEMARK OFFICE
CERTIFICATE OF CORRECTION

PATENT NO. : 3,933,874

DATED : January 20, 1976

INVENTOR(S) : Atsuaki Arai et al

It is certified that error appears in the above-identified patent and that said Letters Patent are hereby corrected as shown below:

Column 2, line 55, delete "R" and insert -- $R_1$ --

Column 4, line 26, delete "atcetonitrile" and insert -- acetonitrile --

Column 5, line 19, delete " amilino" and insert -- anilino --

Signed and Sealed this fourth Day of May 1976

[SEAL]

Attest:

RUTH C. MASON
*Attesting Officer*

C. MARSHALL DANN
*Commissioner of Patents and Trademarks*